United States Patent [19]
Monter et al.

[11] 3,976,055
[45] Aug. 24, 1976

[54] ELECTRODE AND CONDUCTOR THEREFOR

[75] Inventors: Robert Paul Monter; Albert Moore Hall, both of Centerville; James Vernon Cartmell, Dayton, all of Ohio

[73] Assignee: NDM Corporation, Dayton, Ohio

[22] Filed: Nov. 27, 1974

[21] Appl. No.: 527,033

Related U.S. Application Data

[63] Continuation-in-part of Ser. No. 424,959, Dec. 17, 1973, abandoned.

[52] U.S. Cl. ............ 128/2.06 E; 128/2.1 E; 128/417; 128/DIG. 4; 174/68 A; 252/503; 252/511; 252/513; 252/514
[51] Int. Cl.² .......................................... A61B 5/04
[58] Field of Search ............ 128/2.06 E, 2.1 E, 416, 128/417, 418, DIG. 4; 174/68 A; 252/502, 503, 511, 513, 514

[56] References Cited
UNITED STATES PATENTS

| | | | |
|---|---|---|---|
| 1,053,881 | 2/1913 | Scott et al. | 174/68 A |
| 2,580,628 | 1/1952 | Welsh | 128/2.06 E |
| 2,782,786 | 2/1957 | Krasno | 128/417 |
| 3,003,975 | 10/1961 | Louis | 252/503 |
| 3,029,808 | 4/1962 | Kagan | 128/2.06 E |
| 3,083,169 | 3/1963 | Ueda | 252/511 |
| 3,385,677 | 5/1968 | Schreiner et al. | 29/182 S |
| 3,474,775 | 10/1969 | Johnson | 128/2.1 E |
| 3,490,442 | 1/1970 | Streu | 128/2.06 E |
| 3,566,860 | 3/1971 | Moe, Jr. | 128/2.06 E |
| 3,599,629 | 8/1971 | Gordy | 128/2.06 E |
| 3,602,216 | 8/1971 | Moe, Jr. | 128/2.06 E |
| 3,606,881 | 9/1971 | Woodson | 128/2.06 E |
| 3,701,346 | 10/1972 | Patrick, Jr. et al. | 128/2.06 E |
| 3,721,246 | 3/1973 | Landis | 128/404 |
| 3,733,385 | 5/1973 | Reddish | 252/511 |
| 3,760,495 | 9/1973 | Meyer | 252/511 |
| 3,792,700 | 2/1974 | Sarnoff et al. | 128/2.06 E |
| 3,828,766 | 8/1974 | Krasnow | 128/2.1 E |

FOREIGN PATENTS OR APPLICATIONS

| | | | |
|---|---|---|---|
| 1,466,919 | 7/1969 | Germany | 128/2.06 E |

*Primary Examiner*—William E. Kamm
*Attorney, Agent, or Firm*—Dybvig & Dybvig

[57] ABSTRACT

An electrode for sensing signals such as electrocardiograph signals used with an electrolyte is formed from an electrically conductive but galvanicallly inactive material having a galvanically active conductive material at the electrolyte interface. Examples are described including a body formed from a plastic or other non-conductive binder rendered conductive by inclusion of finely divided conductive carbon and having one or more metal particles anchored to the surface of the body which contacts the electrolyte.

38 Claims, 12 Drawing Figures

ELECTRODE AND CONDUCTOR THEREFOR

RELATED APPLICATION

This is a continuation-in-part of our application Ser. No. 424,959 filed Dec. 17, 1973 now abandoned.

BACKGROUND OF THE INVENTION

1. Field of the Invention

The present invention relates to electrodes for sensing signals such as electrocardiograph signals and, more particularly, this invention relates to electrode elements or conductors adapted for use in such electrodes to interconnect an electrolyte with suitable signal processing or monitoring equipment.

2. Description of the Prior Art

U.S. Pat. Nos. 3,696,807 and 3,701,346 illustrate medical electrodes which are known in the prior art and to which the present invention is applicable. In these patents an electrolyte applied to the skin of a human or other animal subject is interfaced to electrocardiograph monitoring equipment by a solid metal conductor such as silver contacted to the electrolyte. Electrodes of this type are known to function adequately to meet the needs of the medical profession but are also relatively expensive because the preferred metal for electrolyte contact is silver. Even though the amount of silver used in such electrodes is not great, the cost of the silver used in the electrode represents a significant cost factor. Aside from the cost of the raw metal, difficulties encountered in forming or shaping solid metal contribute to the cost of electrode manufacture. Because of the cost of the manufacture, commercially available electrode configurations are to some extent limited.

U.S. Pat. No. 3,566,860 teaches an electrode conductor for interconnecting between an electrolyte and electrocardiograph monitoring equipment, the conductor comprising a dispersion of finely divided carbon in plastic. Such a conductor is desirably inexpensive but is also found to be relatively ineffective when compared with electrode devices which utilize metal conductors. In particular it is found that the signal which such an electrode can transmit to associated monitoring equipment is so erratic (wandering base line, irregular trace) that the informational signals available at the skin surface of the subject being monitored are distorted and sometimes entirely obscure.

It has also been known to produce electrode elements comprising a layer of silver on a copper support. Electrocardiograph traces obtained with the use of such electrodes frequently reveal a base line irregularity and the failure to provide proper repetitive wave forms, particularly after an extended period of contact with an electrolyte. Even when great care is employed in producing the silver layer, there is a distinct likelihood that the electrolyte will contact the underlying copper through minute pores in the silver layer. It is believed that when the electrolyte has invaded the silver layer so as to engage the underlying copper, the electrocardiograph monitoring equipment is seeing the product of two electrodes, one being silver contacted by the electrolyte and the other being copper contacted by the electrolyte, and it is further believed that reactions occur between these dissimilar metals which disturb the signals received by the monitoring equipment.

SUMMARY OF THE INVENTION

In accordance with this invention, a biomedical electrode is constructed with an electrode conductor or element comprising a material formed from a first electrical conductor which is galvanically inactive in the presence of an electrolyte and a second electrical conductor which is galvanically active in the presence of an electrolyte, the second conductor being present at the surface which engages the electrolyte. Further in accordance with this invention, a conductor suitable for use in biomedical electrodes is inexpensively fabricated by forming the first mentioned conductor, which is galvanically inactive, from an easily formable material having as little as one minute particle of the second conductor, which is galvanically active, at the surface contacting an electrolyte.

A structurally adequate non-conductive binder material such as a plastic, rubber or ceramic into which is thoroughly dispersed a finely divided electrically conductive carbon is ideally suited for forming the first mentioned, galvanically inactive conductor. The second, galvanically active conductor can be practically any metal. As will be more fully explained in the following description, the quantity of the galvanically active conductor present at the interface between the electrolyte and the galvanically inactive conductor is not critical so long as at least some of the galvanically active conductor is present at the interface. Thus, the present invention teaches that a vanishingly small amount of metal located at the interface between an electrolyte and a plastic rendered conductive by the dispersion of conductive carbon throughout, the metal contacting a portion of the dispersed carbon, can be used to produce an inexpensive but nevertheless fully acceptable electrode element for interconnecting between an electrolyte and measuring or monitoring equipment.

The metal used in this invention is not critical so long as the metal is galvanically active in the presence of the electrolyte. When the electrode is packaged prefilled with an electrolyte, or used for long term monitoring, silver is preferred. Zinc is preferred for electrodes which are to be used for a relatively short duration of time wherein the electrolyte is applied to the electrode immediately prior to use. When more than one metal particle is present at the electrolyte interface, all metal particles should be of the same metal or of alloys having the same chemical composition. The metals present at the interface are preferably substantially pure.

There is practically no limit to the design configuration of electrodes made in accordance with this invention. A variety of non-conductive binders which can be rendered conductive by inclusion of dispersed carbon or other galvanically inactive conductive material are commercially available or can be easily produced which are readily formable as by molding, machining or other operations to any desired shape. In its preferred forms the present invention contemplates that the conductive, but galvanically inactive material is inherently structurally sound or, when formed, has a self supporting shape. However, the invention is not so limited because this material could, for example, be coated on a non-conductive substrate such as plastic.

As will be further described below, there are numerous methods for producing electrode elements in accordance with this invention. The presently preferred method is to disperse a conductive carbon and a metal in the form of powder or small particles throughout a molding resin so as to obtain a homogeneous mixture and then to mold the elements to the desired shape. The weight of dispersed metal to the total weight of the final product can be in the range of at least as small as 0.7% and at least as large as 30% with carbon ranging by weight of final product from 20% to 50% with the remainder a molding resin. The preferred range is approximately 15–30% by weight metal, 25–30% by weight carbon and 40–60% by weight molding resin. With these ranges there is sufficient metal in the mold mix that one or more particles will assuredly be at the surface of the conductor which engages the electrolyte, relatively small quantities of relatively expensive metal are used, and the mix is easily molded to the desired shape.

An object of this invention is to provide an inexpensive conductor for connection between an electrolyte and signal measuring or monitoring equipment.

Another object of this invention is to provide an inexpensive conductor suitable for use in medical electrodes.

Other objects and advantages reside in the construction of parts, the combination thereof, the method of manufacture and the mode of operation, as will become more apparent from the following description.

DESCRIPTION OF THE PREFERRED EMBODIMENTS

Figure 1:
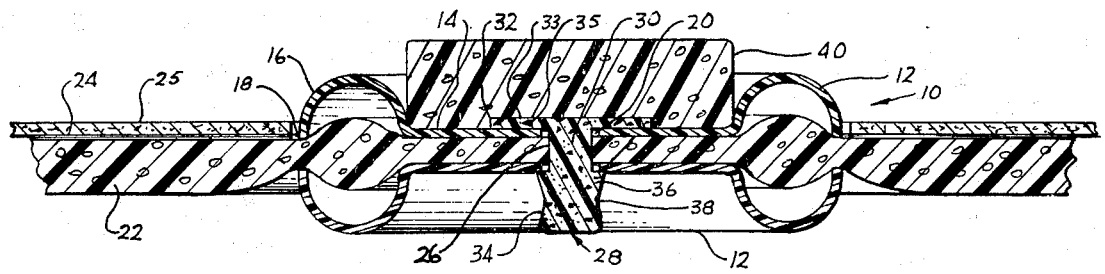
FIG. 1 is a section view of a medical electrode having a conductor fabricated in accordance with the present invention.
Figure 2:
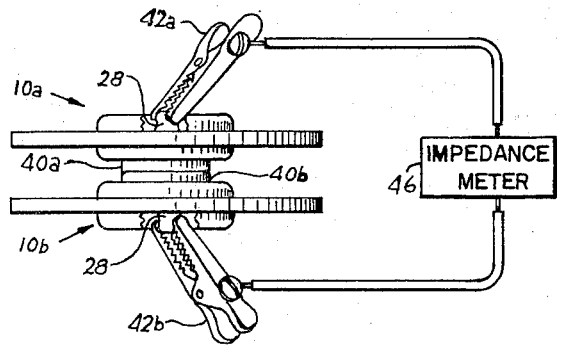
FIG. 2 is an elevation view illustrating one mode in which electrode conductors of the general type shown in FIG. 1 can be tested.

FIG. 1 illustrates an electrode 10 which is of the type shown in FIG. 2 of U.S. Pat. No. 3,969,807 but which has been modified by the inclusion therein of a molded conductor 28, the conductor 28 replacing a two-piece metallic snap fastener which appears in U.S. Pat. No. 3,696,807.

The electrode can be seen to comprise confronting cavity washers 12 which sandwich therebetween a sheet 22 of foam plastic material. Each of the cavity washers 12 is of circular shape and comprises a generally flat central portion 14 and an arched reinforcing bead 16 which encircles the flat portion 14. The bead 16 terminates at its outer edge with a margin 18. Each of the cavity washers 12 has a central perforation 20 to receive the conductor 28.

The cavity washers are each fabricated of a relatively thin, molded plastic sheet material which is substantially collapse resistant.

The aforementioned foam plastic sheet 22 comprises a foamed elastic material such as polyvinylchloride and has a layer of pressure sensitive adhesive 24 applied to one surface thereof and protected before use by a release paper 25. The sheet 22 has a central aperture 26 which is of the same size and which is aligned with the perforations 20 in the cavity washers 12.

The cavity washers 12 are compressed against the central portion of the sheet 22 by means of the one-piece conductor 28. The conductor 28 can be seen to comprise a molded generally cylindrical body 30 having a circular flange 32 providing an enlarged surface 33 at one end thereof and having a head 34 at the other end thereof. The head 34 has a neck portion 38 of reduced diameter located between the outer end of the head 34 and an outwardly flared conical portion 36. The construction is such that the head 34 can be pressed through the aligned perforations 20 and through the aperture 26 in the intervening sheet 22 whereby the central portions of the cavity washers 12 and the central portion of the sheet 22 will be received between the flange 32 and the conical portion 36.

The axial length of the body 30 is such that when the head 34 has been pressed axially through both of the perforations 20, the foam sheet 22 is slightly compressed. This causes the foam sheet to expand against and snugly grip the body 30. As appears in FIG. 1 the conductor 28 also presses the cavity washers 12 against the foam sheet 22 with sufficient force that the foam sheet is pinched between the margins 18 of the cavity washers thus assuring that there is little freedom of movement of the foam sheet 22 relative to the cavity washers.

It can be noted in FIG. 1 that the adhesive 24 on the sheet 22 is located to the same side of the electrode as the surface 33 on the flange 32 of the conductor 28. To allow the electrode to pick up electrocardiographic signals from the skin of a subject being monitored, the electrode may include a pad 40 of cellular material which is soaked with an electrolyte gel or jelly and which contacts the surface 33 of the conductor 28. The pad 40 is somewhat thicker than the depth of the receiving cup formed by the cavity washer 12 which contacts the flange 32 and, accordingly, when the adhesive coated side of the sheet 22 is pressed against a subject's skin the pad 40 is compressed intimately and firmly against the surface 33.

The electrode 10 was desinged with the objective in view of producing an inexpensive electrode in which a plastic rendered conductive by the dispersion therein of conductive carbon could be molded into the shape of the conductor 28 and acceptable performance for electrocardiograph monitoring obtained. As will become apparent from the numerous tests outlined below, the mere dispersion of a conductive carbon in a molded plastic body does not produce an electrode conductor which is considered acceptable for electrocardiographic purposes. As the following examples will reveal, the problem of inadequate performance of a plastic conductor rendered conductive by the dispersion of carbon therethrough is overcome by the simple expedient of providing at least one particle of metal, which may be vanishingly small, at the interface between the plastic conductor and the electrolyte loaded pad 40.

Test Procedures

FIG. 2 illustrates one mode for testing the performance of electrode conductors. Two electrodes labeled 10a and 10b, respectively, are constructed in a substantially identical fashion, the conductors 28 of the two electrodes being as nearly identical as possible. Each electrode is contacted with a separate electrolyte loaded sponge which overlies the surface 33 of its conductor 28. As shown in FIG. 2, the two electrodes are assembled face-to-face with the electrolyte sponge 40a received in the electrode 10a intimately contacting the electrolyte sponge 40b of the electrode 10b. For convenience, one can refer to the end of the conductor of each electrode which contacts an electrolyte sponge as the wet end of the conductor and the headed end of the conductor which does not contact the electrolyte loaded sponge as the dry end of the conductor.

As shown in FIG. 2, the neck portion of the dry end of the conductor for the electrode 10a is gripped with a pinch clip 42a. Likewise, the dry end of the conductor in the electrode 10b is gripped with a pinch clip 42b. An impedance meter 46 is connected between the pinch clips 42a and 42b. Commercially availabe meters suitable for this mode of testing are the Lab-Line Lectro mho-Meter, Model MC-1, Mark IV marketed by Lab Line Industries, Inc. and the Hewlett-Packard Vector Impedance Meter Model 4800A. All impedance measurements described in this application were made at 1000 $H_z$.

While a measurable reduction in the impedance of the conductors and electrolyte sponges assembled as in FIG. 2 generally indicates improved performance when a single electrode assembled with the type of conductor under test would be utilized as a functioning electrocardiograph electrode, the final criterion for the usefulness of the conductors tested was an assessment of the performance of an assembled electrode when contacted at the conductor surface 33 by an electrolyte loaded sponge and mounted by adhesive 24 on a human subject so that the electrolyte sponge bridged the subject's skin to the conductor and electrocardiograph traces could be visually observed. Commercially available monitoring devices suitable for this purpose are the Cardio-Sentinel Model 505-032-050 Monitor manufactured by Mennen-Greatbatch Electronics, Inc. and, where a permanent record is desired, a Hewlett-Packard Electrocardiograph Model 1500B.

Numerous test results are summarized in the following examples.

EXAMPLE I

Finely divided conductive carbon, sold under the name Vulcan XC-72 by the Cabot Corporation of Boston, Massachusetts, was thoroughly dispersed, by means of suitable mixing equipment, in an ethylene vinyl acetate copolymer obtained from U.S. Industrial Chemicals Co., Division of National Distillers & Chemical Corporation, New York, New York, to provide a moldable conductive plastic mixture comprising 70-weight percent of the copolymer and 30-weight percent of the conductive carbon. A plurality of plastic conductors as shown at 28 in FIG. 1 was molded from the mixture.

EXAMPLE II

Electrodes assembled as in FIG. 1 using plastic conductors from EXAMPLE I were contacted with electrolyte sponges and mounted on human subjects. The subject mounted electrodes performed poorly as exemplified by electrocardiographic traces that were irregular in the sense that characteristics common to successive heartbeats were not reproducibly recorded. Such irregularities result from an undesirably high noise level, waveform distortion and sometimes also result from a wandering base line. Two of the electrodes exhibited a face-to-face impedance of 2,685 ohms when tested as shown in FIG. 2.

EXAMPLE III

Plastic conductors from the plurality produced in EXAMPLE I were first softened by heating at one end (surface 33 of FIG. 1) of each conductor and contacted with lead power (100 mesh) with a force sufficient to embed lead particles in the surface 33 of each of the conductors. The amount of lead embedded was approximately 1.2 percent of the initial weight of the conductor. After cooling to room temperature, the conductors with embedded lead were assembled into separate electrodes of the type shown in FIG. 1 and each contacted with a gel impregnated electrolyte sponge, the sponges being contacted to the surface of the conductors having lead power embedded therein. When subject mounted, these electrodes gave electrocardiographic traces that were regular in the sense that waveforms were recorded with reasonable reproducibility, the traces also being reasonably free of base line wandering and background noise. The traces exhibited a clearly noticeable improvement over the performance of the unmodified plastic conductors from EXAMPLE I. The average impedance of several pairs of electrodes with lead powder embedded in the plastic conductors was 406 ohms.

EXAMPLE IV

EXAMPLE III was repeated using, in lieu of lead powder, a silver powder (325 mesh) in the amount of approximately 1.1 percent of the initial part-weight. The electrocardiographic traces obtained from subject mounted electrodes from this EXAMPLE were greatly improved over those traces resulting from electrodes containing the unmodified plastic conductors of EXAMPLE II. The average impedance of several pairs of electrodes with silver powder embedded in the plastic conductors was 326 ohms.

EXAMPLE V

EXAMPLE III was repeated using, in lieu of lead powder, a zinc powder (325 mesh) in the amount of approximately 1.1 percent of the initial part-weight. Again, the quality of the electrocardiographic traces obtained with subject mounted electrodes from this EXAMPLE was greatly improved over traces obtained with electrodes containing the unmodified plastic conductors of EXAMPLE I. The average impedance of several pairs of electrodes with zinc powder embedded in the plastic conductors was 421 ohms.

EXAMPLE VI

The procedure of softening plastic conductors from EXAMPLE I and contacting with metal powder as repeated but with the metals and alloys listed in Table I. Although not all of these materials may be considered useful for biomedical electrode purposes, Table I demonstrates the dramatic decrease in impedance resulting from the presence of a small amount of metal on an electrode element. The weight pickup of metal ranged from 0.3 to 1.8 percent of the weight of the unmodified plastic conductors with an average of about 0.75 percent. Average impedance values at 1000 $H_z$ of assembled face-to-face pairs of electrodes are listed in Table I.

TABLE I

| Metal Powder (Particle Mesh Size) | Avg. Ohms |
| --- | --- |
| None | 2685 |
| Iron (100) | 302 |
| Tin (200) | 351 |
| Aluminum (20) | 435 |
| Nickel (100) | 378 |
| Copper (100) | 308 |
| Chromium (100) | 474 |
| Manganese (60) | 475 |
| Magnesium (100) | 401 |
| Gold (200) | 248 |
| Nickel-Silver (200) nonferrous alloy of Nickel, Copper and Zinc | 428 |
| Stainless Steel 316 (100) | 644 |
| Stainless Steel 304 (100) | 526 |
| Titanium (20) | 392 |
| Bismuth (20) | 299 |
| Cadmium (20) | 259 |

Alternately, the intimate dispersion of conductive carbon in copolymer might vary in composition from 80-weight percent copolymer/20-weight percent carbon to 50-weight percent copolymer/50-weight percent carbon including all possible compositions between the two extremes. Alternately, the copolymer might be replaced with another plastic such as polyethylene, polypropylene, polyvinylchloride, nylon, Teflon, silicone rubber or various copolymers of the above and terpolymers, such as poly (ethylene propylene ethylidene norbornene), which is commonly abbreviated as EPDM.

Alternately, the conductive dispersion above might be replaced with any of several conductive plastic molding compositions both thermoplastic and thermosetting available commercially. We have found the following materials useful: Conductive EPDM composed of approximately 45 percent carbon and 55 percent terpolymer and available from Projects Unlimited, Inc. of Dayton, Ohio. Conductive polyvinylchloride available from Abbey Plastics Corporation, Hudson, Massachusetts. Conductive ethylene vinyl acetate copolymer dispersions of varying carbon content available from U.S. Industrial Chemicals Corporation, New York, New York.

Alternately, the Vulcan XC-72 conductive carbon might be replaced by other commercially available conductive carbon blacks. The electrical resistivity of the carbon employed must be of such magnitude to be considered "low". Carbon blacks fitting such a requirement generally are also characterized by small particle size and "high-structure" as defined in *Encyclopedia of Chemical Technology*, Interscience, New York, 2nd Edition, V4 (1964) pgs. 243–247 and 280–281.

EXAMPLE VII

It is possible to embed metal powder at one end (surface 33 of FIG. 1) of each plastic conductor during the molding operation. In an example, silver powder (325 mesh) was brush applied to selected mold cavity surfaces just prior to molding conductive EPDM composed of approximately 45 percent conductive carbon and 55 percent terpolymer available from Projects Unlimited, Inc. of Dayton, Ohio. The average face-to-face impedance of final electrode assemblies was 186 ohms, whereas that of the plastic conductors not containing added metal was 300 ohms.

EXAMPLE VIII

The metal embedded in the surface of the plastic conductor may also be in the form of small pieces of thin foil or short lengths of fine wire. In this EXAMPLE, a plurality of plastic conductors was molded from a conductive EPDM molding composition consisting of approximately 55 percent terpolymer and 45 percent conductive carbon and available from Projects Unlimited, Inc. of Dayton, Ohio. The shape of the molded conductors was identical to that of EXAMPLE I except that an insert was placed in the mold cavity so that the molded parts each contained a cylindrical indention approximately 1/16 inch in diameter and ¼ inch deep located within surface 33 of the part as identified in FIG. 1.

Platinum metal foil was pressed into the indentations of several plastic conductors from the plurality produced above. The weight of platinum foil was 12.8 percent of the initial weight of the plastic conductors. After electrode assembly and addition of gel impregnated electrolyte sponges, the 1000 $H_z$ impedance of face-to-face pairs was 67 ohms.

Alternately, platinum wire, gold foil, gold wire or silver foil were pressed into plastic conductors in the amounts shown in Table II; impedance values at 1000 $H_z$ are also indicated in Table II.

TABLE II

| Added Metal | Percent Added | Avg. Ohms |
| --- | --- | --- |
| None | — | 300 |
| Platinum Foil | 12.8 | 67 |
| Platinum Wire | 18.5 | 85 |
| Gold Foil | 7.2 | 93 |
| Gold Wire | 2.8 | 84 |
| Silver Foil | 27.8 | 49 |

EXAMPLE IX

A plurality of plastic conductors was molded to the shape of the conductor 28 shown in FIG. 1 from a moldable conductive plastic mixture comprising 60-weight percent of an ethylene vinyl acetate copolymer, obtained from U.S. Industrial Chemicals Co., and 40-weight percent of conductive carbon, identified as Vulcan XC-72 and obtained from the Cabot Corporation. Silver paint identified as SC12 and available from Micro-Circuits Company of New Buffalo, Michigan, was applied to the entire area of surface 33 identified in FIG. 1 of a plurality of the molded conductors, while others of the herein molded conductors were left unpainted, as controls. After allowing sufficient time for the paint to harden (complete evaporation of solvent), a quantity of painted conductors was weighed to determine that approximately 0.6 percent (based on initial part-weights) of silver paint was deposited. The painted conductors, as well as unpainted controls from the same manufacture were then assembled into separate electrodes of the type shown in FIG. 1. When contacted with electrolyte sponges and subject mounted, the painted electrodes gave electrocardiographic traces that represented an improvement over the performance of electrodes containing unpainted conductors from the same manufacture. The impedance of a face-to-face pair of electrodes containing silver painted conductors was 79 ohms, whereas the impedance of electrodes containing unpainted control conductors was 1180 ohms.

Alternately, unpainted plastic conductors from the plurality produced above were painted with silver paint such that only 50 percent of the area of the surface 33 was coated. Alternately, silver paint was applied to several unpainted conductors such that only 25 percent of the surface 33 was coated. Then one small dot of silver paint was applied to the surface 33 of several previously unpainted plastic conductors. The weight determinations of applied silver paint and the face-to-face impedances of assembled electrodes are shown in Table III. All of the conductors painted with silver paint, regardless of the area covered, yielded final electrode assemblies that performed better than unpainted plastic conductor assemblies of the same manufacture when subject mounted electrocardiograms were obtained.

Finally, plastic conductors from the same manufacture were painted with only a small dot of silver paint and then scraped, while viewed through a microscope, to prepare several conductors with only ½ a small dot of silver paint and another set of conductors with only 1/10 a small dot of silver paint. The estimated weights of paint remaining and face-to-face electrode impedances are shown in Table III.

TABLE III

| Area Covered with Silver Paint | Weight Percent Silver Paint | Avg. Ohms |
| --- | --- | --- |
| 0 | 0 | 1180 |
| 100% | 0.60 | 79 |
| 50% | 0.33 | 94 |
| 25% | 0.20 | 96 |
| Small Dot | 0.09 | 260 |
| 1/2 Small Dot | 0.045(estimated) | 360 |
| 1/10 Small Dot | 0.009(estimated) | 420 |

EXAMPLE X

It is possible to produce molded plastic conductors containing metal particles embedded in and visible through a microscope on the surface of the molded conductors by mixing the metal particles into a plastic rendered conductive by carbon prior to the molding operation. This is most easily accomplished by intimately dispersing both a conductive carbon and a metal powder throughout a plastic to be molded so as to obtain an optimum mixture in terms of homogeneity.

In this example, 30 parts by weight Vulcan XC-72 and 15 parts by weight silver powder were thoroughly dispersed within 55 parts by weight of an ethylene vinyl acetate copolymer to provide a moldable conductive plastic mixture. Conductors molded from a mixture comprising 40 parts by weight XC-72 and 60 parts by weight of the ethylene vinyl acetate copolymer, but lacking any added metal were used as controls. A plurality of plastic conductors was molded from the mixture including silver powder and assembled into electrodes as in FIG. 1, then contacted with gel impregnated electrolyte sponges. When subject mounted, these electrodes gave electrocardiographic traces that were regular, free of base line wandering, and free of background noise and represented an improvement over the performance of the control conductors containing no added metal. A typical face-to-face impedance of several pairs of electrodes with silver powder thoroughly dispersed throughout the plastic conductors was 143 ohms, whereas a representative impedance of the control electrodes containing no added metal was 5600 ohms.

Alternately, the silver powder was replaced with other metals and alloys to give the face-to-face electrode impedances shown in Table IV.

TABLE IV

ELECTRODE IMPEDANCES AT 1000 HZ.
55 EVA/30 CARBON/15 METAL CONDUCTORS

| Added Metal | Avg. Impedance Ohms |
| --- | --- |
| None | 5600 |
| Silver (325 Mesh) | 143 |
| Iron (100 Mesh) | 174 |
| Nickel-Silver (200 Mesh) | 800 |
| Stainless Steel 304 (100 Mesh) | 1230 |
| Stainless Steel 316 (100 Mesh) | 1430 |
| Zinc (325 Mesh) | 269 |

EXAMPLE XI

Wide variations in the weight ratios of molding resin to conductive carbon and to metal in the moldable conductive plastic mixture of EXAMPLE X have proven useful. The composition formulations shown in Table V were all molded into conductors and electrodes prepared from the plastic conductors as shown in FIG. 1 gave subject mounted electrocardiographic traces that represented improvements over the performances of the control conductors described in EXAMPLE X.

TABLE V

WEIGHT PERCENT OF MIX COMPONENTS

| Molding Resin | Carbon | Silver Powder |
| --- | --- | --- |
| 41 | 50 | 9 |
| 45 | 40 | 15 |
| 50 | 35 | 15 |
| 51 | 40 | 9 |
| 55 | 30 | 15 |
| 56 | 35 | 9 |
| 56 | 29 | 15 |
| 57 | 28 | 15 |
| 59 | 26 | 15 |
| 61 | 30 | 9 |
| 61 | 24 | 15 |

EXAMPLE XII

The amount of added metal thoroughly dispersed throughout the moldable conductive plastic mixture of EXAMPLE X can constitute less than one percent of the total weight of the mixture. In this EXAMPLE, a mixture of 94-weight percent conductive EPDM molding resin, available from Projects Unlimited, Inc. of Dayton, Ohio, with six-weight percent silver powder was used to prepare a plurality of plastic conductors as in EXAMPLE I. Alternately, mixtures of 3-weight percent silver/97-weight percent resin and 0.7-weight percent silver/99.3-weight percent resin were similarly prepared.

Electrodes assembled with gel impregnated electrolyte sponges and subject mounted gave electrocardiographic traces, in the case of all three of the above formulations, that represented improvements over the performance of plastic conductors containing no added metal.

EXAMPLE XIII

The practical upper limit of added metal thoroughly dispersed throughout the moldable conductive plastic mixture of EXAMPLE X is not known, but can constitute at least 30-weight percent of the total weight of the mixture. In this example, a series of conductive plastic mixtures was prepared wherein the weight ratio of an ethylene vinyl acetate molding resin to conductive carbon dispersed therein remained relatively constant, and the amount of dispersed zinc powder was varied from as low as 15-weight percent to as high as 30-weight percent of the total weight of the mixture.

After molding into the shape of plastic conductors and assembled as shown in FIG. 1 into electrodes then contacted by electrolyte sponges to human subjects, electrocardiographic traces were obtained in all cases that represented improvements over the performance of plastic conductors containing no added metal. As shown in Table VI, the impedance values of face-to-face electrode pairs reflected the amount of metal in the mix; increasing amounts of metal giving decreasing impedance value.

TABLE VI

| Weight Percent | | | Avg. Impedance |
|---|---|---|---|
| EVA Resin | Carbon | Zinc Powder | Ohms |
| 55 | 30 | 15 | 1250 |
| 52 | 28 | 20 | 700 |
| 50 | 28 | 22 | 530 |
| 45.2 | 24.8 | 30 | 195 |

In all EXAMPLES except EXAMPLE XIII, the electrolyte solution comprised a mixture of water, a water swellable mucilage and 7% sodium chloride based on the weight of the electrolyte solution. In EXAMPLE XIII the electrolyte solution comprised a mixture of water, a water swellable mucilage and 15% sodium sulfate based on the weight of the electrolyte solution.

The deficiencies in electrodes made from dissimilar, unalloyed metals, such as electrode elements having a silver layer over copper, are not encountered in the use of electrodes made in accordance with this invention. Although not fully understood, this benefit may result from the fact that the conductive plastic is a galvanically inert substance which does not interact electrolytically with the electrolyte. The metal thus need not form a complete partition between the electrolyte and the conductive plastic and therefore the amount of metal present at the electrolyte interface can be exceedingly small. For whatever reasons, medical electrodes using the conductors made in accordance with this invention when used with conventional electrolytes and ordinary commercially available monitoring equipment produce signal traces having highly stable base lines as well as regular and repetitive wave forms.

Metals are frequently distinguished from non-metallic elements or compositions by their conductivity and ability to form positive ions. This line of distinction applies to all of the metals, including alloys, described in the foregoing examples. The foregoing examples accordingly reveal that the presence of any metal which is securely affixed to or embedded in the surface 33 of the conductor 28, thus contacting some of the conductive carbon distributed throughout the conductor 28, will be effective when contacted to a compatible electrolyte loaded into the sponge 40 to materially enhance the performance of the electrode. The selected metal and the selected electrolyte will usually cooperate to produce enhanced performance, and hence be considered compatible, if the metal is galvanically active when contacted to the electrolyte and applied to the skin of a subject. As discussed below, the selection of the metal and the electrolyte will depend upon the intended use of the electrode and any selected metal-electrolyte combination must be tested under actual conditions of use for its particular characteristics.

In some applications, such as respiration rate measurement, the relatively low impedance obtained with electrodes in accordance with this invention is the primary benefit. For electrocardiographic purposes, the metal-electrolyte combination should function in the sense that a stable base line as well as regular and repetitive wave forms are produced. The tests to date suggest that any metal lodged at the interface of the conductive plastic gives improved results when compared to a conductive plastic without metal. However, the permanency of such improved results, and the magnitude of improvement that can be observed, is influenced by the character of the metal and the electrolyte used. For example, aluminum and stainless steel particles are not compatible with sodium chloride electrolytes for use in electrocardiograph monitoring because irregular patterns are formed. Sodium sulfate electrolytes are, however, compatible with both aluminum and stainless steel for electrocardiograph purposes.

Silver is found particularly useful in "prefilled" electrodes made in accordance with this invention in which the electrode is packaged with an electrolyte-loaded sponge material engaging the electrode conductor. The preferred electrolytes for use with silver are sodium chloride solutions. Such electrodes are reasonably stable over long periods of time if first aged in the package for a period of hours or days while the metal remains in contact with the electrolyte. In addition to convenience offered by prefilling with electrolyte, these electrodes have been found excellent for long term monitoring.

An electrode made in accordance with this invention wherein the galvanically active conductive material is zinc has proven highly desirable for "dry" electrodes. In use, a dry electrode is packaged without an electrolyte, the electrode being contacted with the electrolyte immediately prior to use. Electrodes having a conductor formed from zinc particles in a conductive plastic made in accordance with this invention has been found to develop a stable base line for electrocardiograph purposes immediately following contact with either a sodium chloride or a sodium sulfate electrolyte. However, base line stability is not reliably maintained beyond a period of several hours or days. Accordingly, electrodes with zinc manufactured in accordance with this invention should not be prefilled.

When more than one metal particle is present at the electrolyte interface, it is preferred that all metal particles be of the same metal or alloys of the same chemical composition. If dissimilar, unalloyed, metals are present at the electrolyte interface, base line instability is encountered with the result that regular electrocardiograph traces are not obtained. For the same reasons, the metals or alloys present at the electrolyte interface are preferred to be substantially pure.

FIG. 1 illustrates as a preferred embodiment the dispersion of metal particles 35 throughout the body of the conductor 28. This embodiment is presently preferred because of convenience in manufacture since the conductive plastic and metal particles can, after premixing, be molded in one operation. Any of the previously described conductors having the various described ranges by weight of dispersed metal particles can be used. Approximately 15% by weight metal particles is presently preferred when the metal is silver because we have found that sufficient particles will be then present in the mold mix that, invariably, several particles will be present at the interface. A higher percentage of silver particles will not materially enhance the stability of electrode operation and will increase cost. When the metal is zinc, approximately 30% by weight metal particles is presently preferred. The higher zinc content results in a longer period of stability during use. Significantly higher percentages of metal particles may create difficulties in molding.

It is to be understood, of course, that the conductor 28 also includes finely divided conductive carbon dispersed throughout the body of the conductor. No attempt has been made to particularly illustrate the carbon particles. For adequate conductivity and good molding properties, the preferred range of carbon to weight of final product is 25–30% and molding resin by weight is 40–60%.

The foregoing examples show it sufficient for the purposes of satisfactory electrode operation that only one of the metal particles dispersed throughout the conductor 28 be lodged at the interface between the conductor surface 33 and the electrolyte sponge 40.

Figure 3:
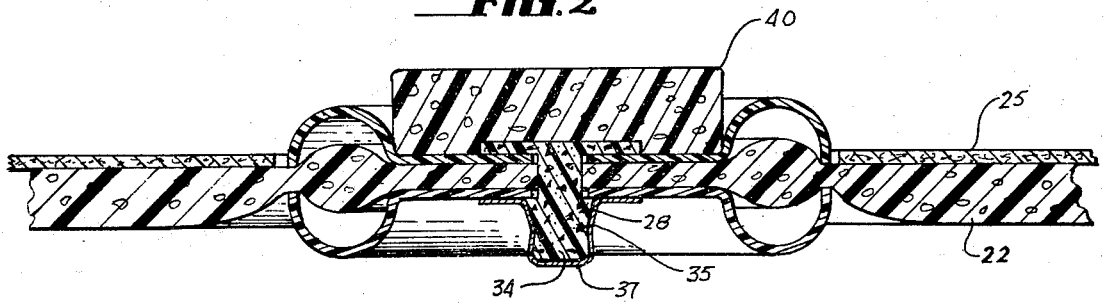
FIG. 3 is a section view illustrating a first modification.

FIG. 3 illustrates a modification of the preferred embodiment in which the conductor 28 has been press-fitted into a conventional snap fastener part 37. For the operation of this embodiment it is unimportant whether the snap fastener part 37 contacts any of the embedded metal. It is only important that the part 37 intimately engage the conductor 28.

The snap fastener part 38 provides a convenient means for connecting the electrode of the preferred embodiment to monitoring equipment already commercially available.

Figure 4:
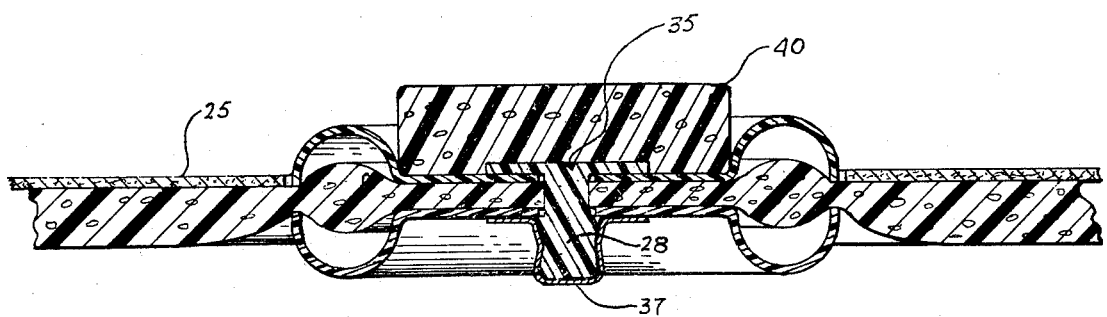
FIG. 4 is a section view illustrating a second modification.

FIG. 4 illustrates a further modification in which the conductor 28 is again protected by a conventional snap fastener part 37 and, to show one extreme of the present invention, only a single metal particle 35 has been anchored to the surface 33 of the conductor 28.

Again it is to be understood that, while not specifically illustrated, the conductor in all figures of the drawing comprises a plastic through which has been dispersed finely divided conductive carbon. Other formable nonconductors, such as rubber or ceramics, made conductive by included carbon may also be used with a metal which is galvanically active. At present, carbon is thought to be the only available conductive material which can be dispersed through a nonconductor to produce a galvanically inactive conductor. However, if other such materials may be or may become available, they would be useful in the practice of this invention.

It will occur to those skilled in the art that the conductor 28, while described as a part separate from the cavity washer or cup member 12 which receives the flange 32 may, in fact, be formed as one piece with the cavity washer 12. Inasmuch as the best electrical path between the conductor 28 and the skin of a subject will be the path provided by the electrolyte, it will be unimportant if the cavity washer 12 is also conductive and of the same composition as the conductor 28. Thus, it is entirely feasible within the scope of the present invention to form the upper cavity washer 12 in FIG. 1 as one piece with the conductor 28.

FIGS. 5–12 illustrate other forms of medical electrodes utilizing the present invention. These figures of the drawing give a partial indication of the wide variety of medical electrode constructions made possible by this invention.

Figure 5:
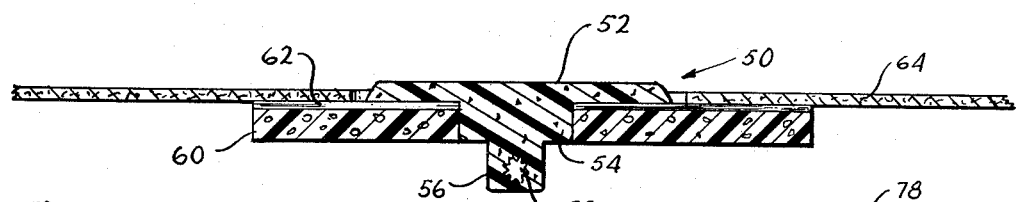
FIG. 5 is a section view illustrating a third modification.
Figure 6:
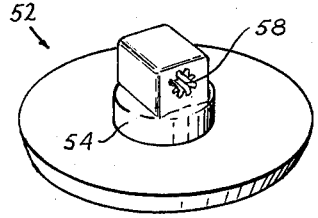
FIG. 6 is a perspective view of the conductive electrode element of FIG. 5.

FIGS. 5 and 6 illustrate an electrode assembly 50 with a one-piece disc-shaped conductor 52 having a projecting hub portion 54 from which, in turn, projects a central stub or head 56. The stub 56 han an internally splined hole 58 adapted to receive a jack or other electrical connection to external monitoring equipment. Hub portion 54 is surrounded by a circular foam plastic pad 60 having an adhesive layer 62 engaging a removable cover sheet sheet 64. The adhesive layer 62 is also in contact with the face of the disc portion of the conductor 52 surrounding the hub 54. As will be apparent to those familiar with the electrode art, the electrode assembly 50 can be very inexpensively manufactured especially since the conductor 52 with its hub 54 and stub 56 can be molded in one piece from a plastic rendered conductive by included carbon and with a modest percentage of metal particles. The electrode 50 is intended to be a so-called dry electrode. In use the electrolyte is applied to the exposed face of conductor 52 immediately prior to use. The metal preferred in construction of the conductor 52 is zinc because, as explained above, zinc is the preferred metal for dry conductors.

Figure 7:
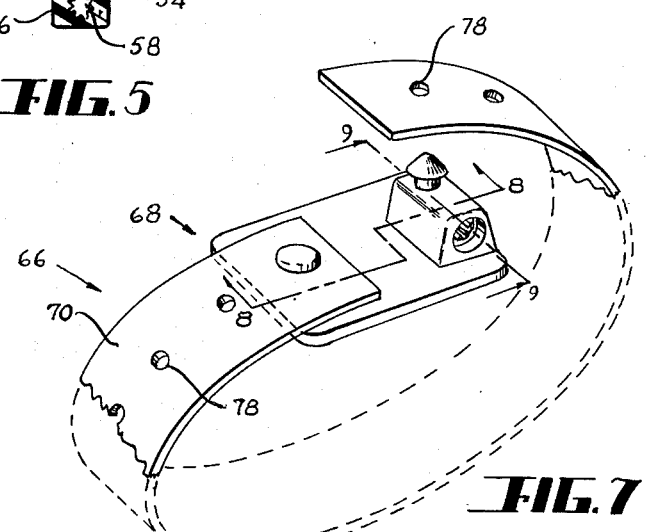
FIG. 7 is a perspective view of a fourth modification.
Figure 8:
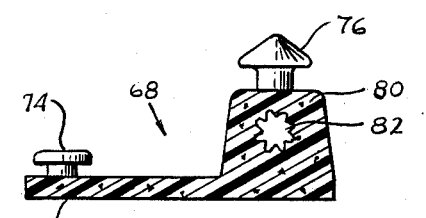
FIGS. 8 and 9 are section views taken along lines 8—8 and 9—9, respectively, of FIG. 7.
Figure 9:
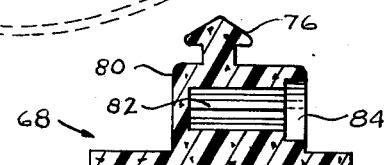

FIGS. 7, 8 and 9 disclose an electrode assembly generally designated 66 having a one-piece conductive plate generally designated 68 of a type adapted to be applied to a limb of a patient by a rubber or plastic strap 70. For convenience of assembly to the strap 70, plate 68 is provided with a first upstanding button or lug 74 and a second upstanding button or lug 76. Lugs 74 and 76 are adapted to be received within apertures 78 extending the length of the strap 70. The second button 76 is mounted on top of a female contact member or head 80 which is molded or otherwise formed integrally as part of the plate 68. Contact member 80 has a splined jack receiving hole 82 which at its exposed end is surrounded by a counterbore 84, the purpose of which will be described below in connection with FIG. 11. Again in accordance with this invention the plate 68 has at least one metal particle at the electrolyte contacting surface 72. Electrode assemblies having upstanding lugs or buttons are not new, one type being shown, for example, in U.S. Pat. No. 2,895,479 granted to R. A. Lloyd on July 21, 1959. However, the advantages of constructing such an electrode assembly with a one-piece molded member rather than from metal are readily apparent.

Figure 11:
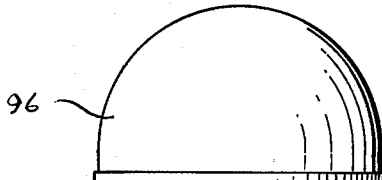
FIG. 11 is a perspective view of the conductive electrode element of FIG. 10.
Figure 11:
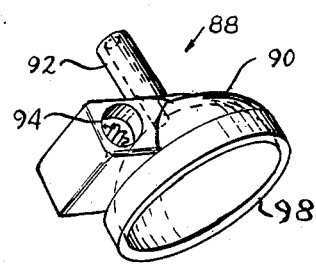
Figure 10:
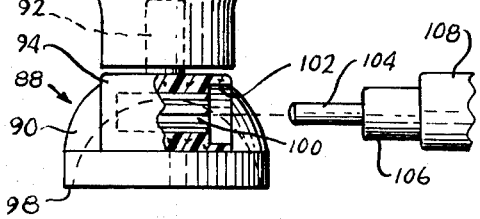
FIG. 10 is a perspective view of a fifth modification and further illustrating a connecting portion of an external conductor for use therewith.

FIGS. 10 and 11 disclose a novel form of suction electrode generally designated 86 having a one-piece electrode conductor generally designated 88. Conductor 88, as best illustrated in FIG. 11, comprises a substantially hemispherical cup 90 with a hollow tubular projection 92 opening to the cup 90 and a female electrical connector portion 94.

The tubular projection 92 tightly fits within the neck of a resilient hollow bulb 96 to thus establish communication for air flow between the inside of the bulb 96 and the cup 90. In use, an electrolyte gel is smeared on the peripheral edge 98 of the cup 90 or on the patient and the bulb 96 is squeezed. The edge 98 is then engaged with the skin and the squeezed bulb released, whereupon a partial vacuum is created in the cup 90 to maintain it in firm electrical contact with the electrolyte covering the skin.

The female connector portion 94 has a splined hole 100 opening to a counterbore 102 for receiving a jack conductor pin 104 which, as conventional, is surrounded by an insulator having a first, smaller diameter portion 106 and a second, larger diameter portion 108. The internal diameter of the splined portion 100 is such that the pin 104 is snugly received therein in secure engagement with the conductive plastic from which the splines are formed. The diameter of the counterbore 102 is only slightly larger than the diameter of the jack insulator portion 106 so that, when the pin 104 is inserted into the hole 100, the insulator portion 106 is received within the counterbore 102 and effectively seals off the hole 100. Because of this design, there is little likelihood that the electrolyte used with the cup periphery 98 can accidentally contact the conductive pin 104. As those familiar with the art understand, contact between an electrolyte and the external conductor is avoided because of the additional galvanic reaction which will occur in the event such contact were made.

Of course, suction electrodes are not new. The suction electrode 86 of this invention, however, is considerably less expensive yet offers the full advantage of conventional suction electrodes. A prior suction electrode is shown in Welsh patent No. 2,580,628 granted by the U.S. Pat. Office on Jan. 1, 1952. The suction cup electrode 86 of the instant invention is most similar to the electrode illustrated in FIG. 3 of the aforementioned Welsh patent. However, whereas the Welsh device requires four metal parts, namely the Welsh cup 35, connector 37, a clamp 39 and a thumb screw for the clamp, all of which parts must be machined and polished, the one-piece molded member 88 of the instant invention performs all of the functions of the above identified parts and, in addition, provides, by virtue of the insulator part 106 surrounding the jack pin 104, a structure for positively preventing accidental contact between the electrolyte and the jack pin. The counterbore 84 of female connector part 80 of the electrode assembly illustrated in FIGS. 7–9 is for the same purpose.

The suction electrode 86 is illustrated in FIGS. 10 and 11 as larger than actual normal size. Although the electrolyte contacting surface 98 is quite small, suction electrodes 86 in accordance with this invention are quite satisfactory in operation because, as already noted, only a very small metal particle need be present at the edge 98 for proper operation. Suction electrodes have been successfully tested in which the conductor 88 is made with dispersed metal particles as are other electrodes described above.

Figure 12:
FIG. 12 is a section view of a sixth modification.

FIG. 12 illustrates yet another electrode assembly 110 consisting only of a single piece of conductive plastic with dispersed metal in accordance with this invention in which a metal conductor 112 for connection to a remote monitoring device is embedded. The area of the piece 110 surrounding the portion thereof receiving the embedded metal conductor 112 is covered by a hot melt insulator 114. This type of electrode can, for example, be applied directly to the back of a patient who is bedridden or an adhesive member (not shown) can be used to hold the assembly in contact with the patient. The metal conductor 112 can extend directly to the monitoring equipment or can have an external connector (not shown) for connection to another conductor. It may be embedded in the conductive plastic part 110 during molding or by other methods.

While the present invention has been described in reference to its utility in medical electrodes such as used in the production of electrocardiographic traces, it is to be understood that the conductor of the present invention is suitable for use in any application wherein the conductor is to be bridged to a source of periodically varying signals by an electrolyte contacted to at least one metal particle embedded in or otherwise anchored to a surface of the conductor.

Although the presently preferred embodiments of this invention have been described, it will be understood that various changes may be made within the scope of the appended claims.

We claim:

1. A conductor adapted to be bridged to a source of periodically varying signals by an electrolyte contacted to one surface of said conductor and also contacted to said source, said conductor comprising:
a first conductor material and a second conductor material contacting said first conductor material, said first conductor material being galvanically inactive, said second conductor material being galvanically active and being anchored to and exposed at said surface.

2. The combination of claim 1 wherein said first conductor material comprises a non-conductive binder rendered conductive by inclusion of electrically conductive carbon dispersed therethrough.

3. The conductor of claim 2 in which said electrically conductive carbon is present in the amount of 20 to 50-weight percent of said conductor.

4. The conductor of claim 1 wherein said second conductor material is metal.

5. The conductor of claim 4 in which said metal comprises at least one metal particle embedded in said surface.

6. The conductor of claim 1 in which said first conductor material comprises a plastic body formed from a non-conductive binder rendered conductive by inclusion of electrically conductive carbon dispersed therethrough and in which said plastic body has plural metal particles dispersed therethrough, said one metal particle being one of said plural metal particles.

7. The conductor of claim 6 in which said metal particles are silver particles.

8. The conductor of claim 7 in which the concentration of silver particles in said conductor is in the range of 0.7 to 30-weight percent.

9. The conductor of claim 7 in which the concentration of silver particles in said conductor is approximately 15-weight percent.

10. The conductor of claim 6 in which said metal particles are zinc particles.

11. The conductor of claim 10 in which the concentration of zinc particles in said conductor is approximately 30-weight percent.

12. The conductor of claim 6 wherein a portion of said first conductor material is located at said surface.

13. The conductor of claim 5 wherein a portion of said first conductor material is located at said surface.

14. The conductor of claim 1 in which said first conductor material comprises a body of plastic rendered conductive by included carbon, and said second conductor material comprises a metal adhered to said surface.

15. The conductor of claim 1 wherein said second conductor material comprises a metal paint.

16. An electrode for use in sensing periodically varying signals, said electrode comprising a formed body of non-conductive material rendered conductive by inclusion of galvanically inactive conductive particles dispersed therethrough, electrolyte means engaged with a surface of said body, said body having a particle of galvanically active conductive material anchored thereto contacting a portion of said conductive particles and contacting said electrolyte means, and means spaced from said surface for electrically connecting said body to signal monitoring equipment.

17. The electrode of claim 16 in which said body has plural metal particles dispersed therethrough, said particle of galvanically active conductive material anchored to said body comprising one of said plural metal particles.

18. The electrode of claim 16 wherein said means spaced from said surface includes a metal snap fastener part seized to said body.

19. The electrode of claim 16 in which said electrolyte means comprises a pad of cellular material soaked with electrolyte jelly.

20. An electrode for use in sensing periodically varying signals, said electrode comprising a formed body of non-conductive material, said body having a portion shaped for connection to signal monitoring equipment, a galvanically active conductive element anchored to a surface of said body spaced from said portion, means including conductive but galvanically inactive material dispersed in said body to provide electrical communication between said portion and said element, and electrolyte means contacting said element for bridging said element to a source of the periodically varying signals to be sensed.

21. In a medical electrode of the type having an electrode element, said electrode element having a surface portion for engagement with an electrolyte and means spaced from said surface portion for connection to monitoring equipment through an external conductor, the improvement wherein said electrode element comprises a formed non-conductive piece loaded with a dispersion of conductive but galvanically inactive particles, and galvanically active conductive means anchored to and exposed at said surface portion and engaging a portion of said dispersed conductive particles.

22. The improvement of claim 21 wherein said dispersed particles are carbon.

23. The improvement of claim 21 wherein said galvanically active conductive means comprises a metal particle.

24. The improvement of claim 23 wherein said metal particle is silver.

25. The improvement of claim 23 wherein said metal particle is zinc.

26. The improvement of claim 21 wherein said metal particle is a substantially pure metal and wherein there is no metal other than the same substantially pure metal exposed at said surface portion.

27. The improvement of claim 21 wherein said electrode element is molded from a mix having 0.7 to 30 percent by weight metal particles, said galvanically active conductive means being at least one of the particles in the mix from which said member is molded.

28. The improvement of claim 27 wherein said metal particles are substantially pure silver.

29. The improvement of claim 27 wherein said metal particles are substantially pure zinc.

30. The improvement of claim 21 wherein said electrode element is formed to comprise a generally cylindrical body having a circular flange at one end thereof and a head at the other end thereof, said surface portion comprising the surface of said flange opposite said head, and said means for connection to monitoring equipment including said head.

31. The improvement of claim 30 wherein said means for connection to monitoring equipment further includes a metal snap fastener part into which said head is press fitted.

32. The improvement of claim 30 wherein said head is provided with a hole for receiving a conductive jack for connection to external monitoring equipment.

33. The improvement of claim 21 wherein said electrode element is disc-shaped with a projecting hub portion from which projects a central stub having a hole adapted to receive a conductive jack.

34. The improvement of claim 21 wherein said electrode is formed as a suction cup having means for connection to an external connector and means for connection to a resilient bulb.

35. A conductor comprising: a homogeneous mixture including a non-conductive binder, conductive, galvanically inert particles dispersed throughout said binder, and metal particles dispersed throughout said binder, at least one of which is exposed at a surface thereof, said inert particles and metal particles being present in the amount of 20 to 50-weight percent inert particles and 0.7 to 30-weight percent metal particles.

36. The conductor of claim 35 wherein said inert particles are carbon present in the amount of 25 to 30-weight percent and said metal particles are substantially pure silver present in the amount of approximately 15-weight percent.

37. The conductor of claim 35 wherein said homogeneous mixture is molded.

38. The conductor of claim 35 wherein said inert particles are carbon present in the amount of 25 to 30-weight percent and said metal particles are substantially pure zinc present in the amount of approximately 30-weight percent.

* * * * *